United States Patent
Yedur et al.

(10) Patent No.: US 6,265,190 B1
(45) Date of Patent: *Jul. 24, 2001

(54) SUCCINIC ACID PRODUCTION AND PURIFICATION

(75) Inventors: Sanjay Yedur, Santa Clara, CA (US); Kris A. Berglund; Dilum D. Dunuwila, both of Okemos, MI (US)

(73) Assignees: Michigan State University, East Lansing; Applied CarboChemicals, Inc., Alto, both of MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/389,641

(22) Filed: Sep. 2, 1999

Related U.S. Application Data

(62) Division of application No. 09/134,061, filed on Aug. 13, 1998, now Pat. No. 5,958,744
(60) Provisional application No. 60/056,013, filed on Aug. 18, 1997.

(51) Int. Cl.[7] ................. C12P 7/46; C12P 1/20; C12P 1/04
(52) U.S. Cl. .............. 435/145; 435/170; 435/252.1; 435/822
(58) Field of Search .................. 435/145, 170, 435/822, 252.1; 562/590, 593

(56) References Cited

U.S. PATENT DOCUMENTS

| 5,143,833 | 9/1992 | Datta . |
| 5,143,834 | 9/1992 | Glassner et al. . |
| 5,168,055 | 12/1992 | Datta et al. . |
| 5,504,004 | 4/1996 | Guettler et al. . |
| 5,573,931 | 11/1996 | Guettler et al. . |
| 5,723,322 | * 3/1998 | Guettler et al. ............... 435/145 |

* cited by examiner

*Primary Examiner*—Herbert J. Lilling
(74) *Attorney, Agent, or Firm*—Stroock & Stroock & Lavan LLP

(57) ABSTRACT

A highly efficient process for the production and recovery of pure succinic acid from a succinate salt that involves minimal use of additional reagents, and produces virtually no waste by-products, and permits internal recycle of the base and acid values, is provided. The method involves the formation of diammonium succinate, either by using an ammonium ion based material to maintain neutral8 pH in the fermenter or by substituting the ammonium cation for the cation of the succinate salt created in the fermenter. The diammonium succinate can then be reacted with a sulfate ion, such as by combining the diammonium succinate with ammonium bisulfate and/or sulfuric acid at sufficiently low pH to yield succinic acid and ammonium sulfate. The ammonium sulfate is advantageously cracked thermally into ammonia and ammonium bisulfate. The succinic acid can be purified with a methanol dissolution step. Various filtration, reflux and reutilization steps can also be employed.

25 Claims, 3 Drawing Sheets

SUCCINIC ACID PRODUCTION AND PURIFICATION

CROSS REFERENCE TO RELATED APPLICATIONS

This is a Divisional Application based on Ser. No. 09/134,061, filed Aug. 13, 1998, now U.S. Pat. No. 5,958,744 which is a continuation-in-part of Provisional Application Ser. No. 60/056,013, filed Aug. 18, 1997 entitled IMPROVEMENTS IN SUCCINIC ACID PRODUCTION AND PURIFICATION, the contents of which are incorporated herein by reference.

BACKGROUND OF THE INVENTION

The invention relates generally to production and purification of organic acids and more particularly to an improved processes for the production and purification of succinic acid from succinate salts that result from the fermentation of carbohydrates.

Succinic acid [110-15-6] (butanedioic acid), $C_4H_6O_4$, is a naturally occurring constituent in plant and animal tissues, see, e.g., Winstrom, L. O. "Succinic Acid and Succinic Annydride", Kirk and Othmer Encyclopedia of Chemical Technology, Vol. 1, $4^{th}$ Ed., (1978), the contents of which are incorporated herein by reference. It has therefore been affirmed as GRAS by the FDA. This status enables it to be used for various purposes, such as, but not limited to, a flavor enhancer, a pH control agent in foods such as condiments and for use in meat products. It is also widely used in scientific applications including uses in radiation dosiometry, standard buffer solutions, agriculture, foods, medicines, cosmetics, textiles, plating and waste-gas scrubbing.

Numerous patents discuss the production of carboxylic acids, such as succinic acid via fermentation. (See, e.g. U.S. Pat. No. 5,168,055 to Datta, the contents of which are incorporated herein by reference.) However, a major factor involved in industrial scale production using fermentation is the cost involved in downstream processing necessary to concentrate and purify the product. For example, it has been determined that fermentation proceeds best at an approximately neutral pH. However, the acid produced will eventually lower the pH. In order to avoid low pH fermentation broths that are injurious to the microorganisms driving the fermentation process, the pH of the broth should be raised by the addition of a base. However, the added basic material generally reacts with the acid and leads to the production of a salt of the carboxylic acid rather than the desired free acid product itself.

Thus, downstream processing typically involves both conversion of the salt into the free acid and the purification of the acidified product. Additionally, insoluble materials from the fermenter, such as the dead cells, generally need to be removed. Therefore, for fermentation to be economically viable, a technique for the production of relatively pure acid and an efficient recovery process is desirable.

U.S. Pat. No. 5,168,055 to Datta et al., the contents of which are incorporated herein by reference, proposed a process that combines the fermentation of carbohydrates to produce calcium succinate and the subsequent conversion to and purification of the succinic acid product. The succinate salt is acidified into the pure acid with sulfuric acid and gypsum, $CaSO_4$, is produced as a by-product. The succinic acid produced is then processed through a series of steps designed to purify the product. However, it has been found that for every mole of succinic acid product produced, an equal amount of gypsum by-product is produced. This gypsum by-product has little value, in part, because the odor and color contamination from the fermentation process renders it unsuitable for commercial use. In addition, reagents such as calcium oxide or calcium hydroxide and sulfuric acid are consumed and are not regenerated within the process.

U.S. Pat. No. 5,143,834 to Glassner et al., the contents of which are incorporated herein by reference, proposes a similar combination of fermentation and purification processes for the production of succinic acid from disodium succinate that is formed in the fermentation step. Succinic acid is produced by using a combination of electrodialysis and water splitting steps that ultimately separate the base, and produce pure acid. Further purification is achieved by passing the product stream through a series of ion-exchange columns. However, this process has disadvantageously high costs, such as membrane costs and the electrical energy costs associated with electrodialysis.

U.S. Pat. No. 5,034,105 to Berglund et al., the contents of which are incorporated by reference, proposes a process for obtaining a carboxylic acid of high purity by using water splitting electrodialysis to convert an undersaturated aqueous solution of disodium succinate into a supersaturated solution of succinic acid that facilitates in crystallizing the product carboxylic acid. However, this process also suffers from the high costs associated with the Glassner et al. patent.

Accordingly, it is the objective of this invention to provide an improved method of producing and purifying carboxylic acids, such as succinic acid, which result from fermentation processes.

SUMMARY OF THE INVENTION

Generally speaking, in accordance with the invention, a highly efficient process for the production and recovery of pure succinic acid from a succinate salt that involves minimal use of additional reagents, and produces virtually no waste by-products, and permits internal recycle of the base and acid values, is provided. The method involves the formation of diammonium succinate, either by using an ammonium ion based material to maintain neutral pH in the fermenter or by substituting the ammonium cation for the cation of the succinate salt created in the fermenter. The diammonium succinate can then be reacted with a sulfate ion, such as by combining the diammonium succinate with ammonium bisulfate and/or sulfuric acid at sufficiently low pH to yield succinic acid and ammonium sulfate. The ammonium sulfate is advantageously cracked thermally into ammonia and ammonium bisulfate. The succinic acid can be purified with a methanol dissolution step. Various filtration, reflux and reutilization steps can also be employed.

Accordingly, it is an object of the invention to provide an improved method and system for producing and purifying succinic acid.

Another object of the invention is to provide an improved method for producing and purifying succinic acid which does not consume substantial quantities of reagents nor produce substantial quantities of by-products.

Still other objects and advantages of the invention will in part be obvious and will in part be apparent from the specification and drawings.

The invention accordingly comprises the several steps and the relation of one or more of such steps with respect to each of the others, and the composition possessing the features, properties, and the relation of constituents, which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
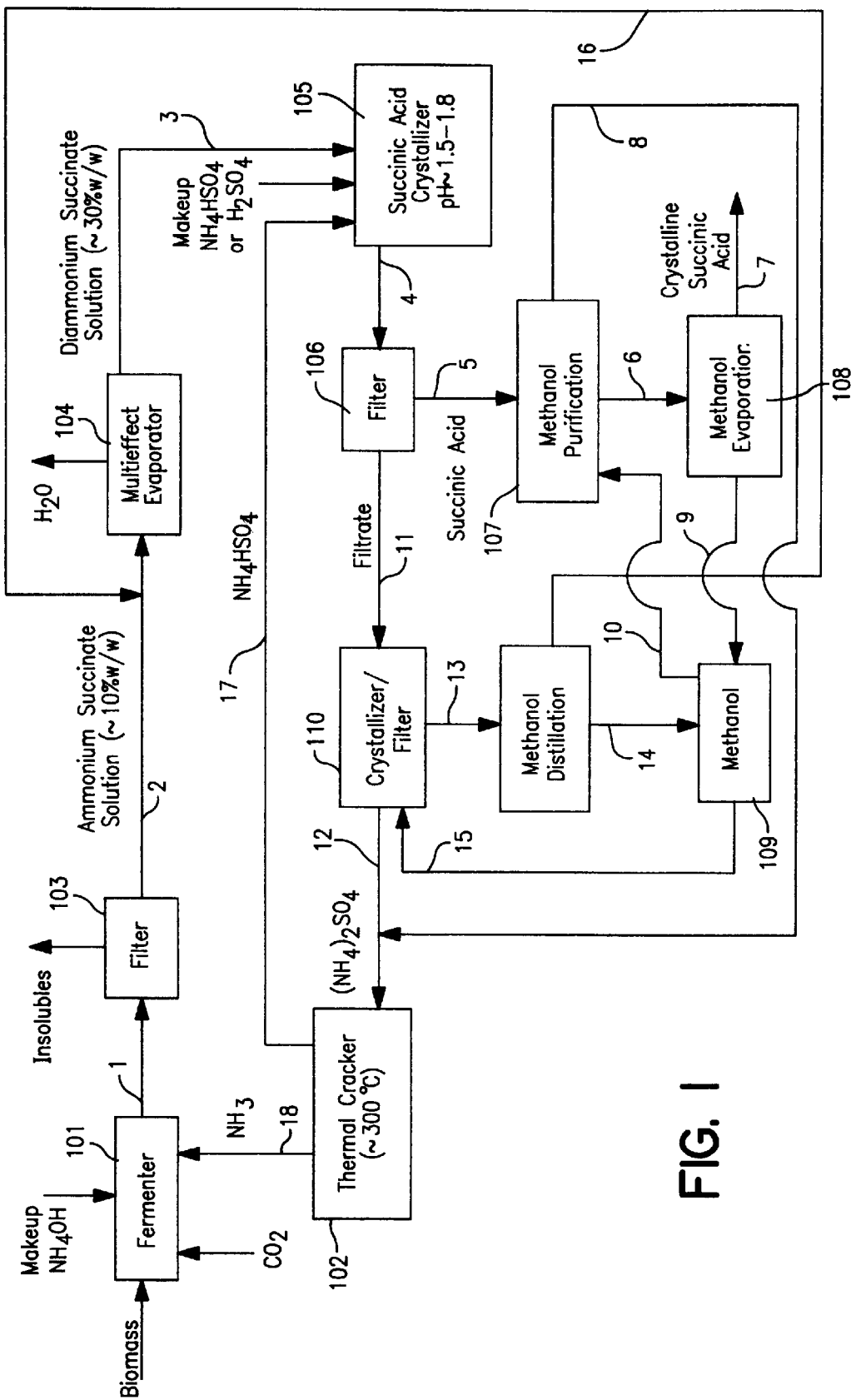
FIG. 1 is a schematic block process flow diagram for the production of succinic acid from diammonium succinate, in accordance with a preferred embodiment of the invention.

The invention provides an advantageous method of producing and purifying succinic acid, based, in part, on the realization that an ammonium sulfate by-product of the purification method can be recycled, to yield a method of production which is substantially free of unwanted by-products and does not require substantial consumption of reagents.

Certain biological materials will produce succinic acid upon fermentation. As acid is produced, the pH of the fermentation broth will steadily decrease, until conditions become intolerable for the biological material. The fermentation broth is advantageously maintained at a pH of over about 6, more preferably at about 7. One way of increasing yield, is to raise the pH (i.e., maintain a substantially neutral pH) by the addition of a base. However, the base will generally react with the succinic acid formed and yield a succinic acid salt, formed of the cation of the base and the succinate anion.

A first step in the production and purification method is to produce diammonium succinate. This can be produced by adding basic material formed with an ammonium ion. A second route to diammonium succinate is to add a different base to the fermentation broth, such as sodium hydroxide and then substitute the ammonium ion for the sodium ion. While most bases are suitable, it has been found that divalent bases, such as calcium hydroxide can lead to certain solubility problems downstream. Accordingly, the monovalent bases (e.g., alkali metal bases), such as sodium hydroxide and potassium hydroxide are preferred.

The salt of the base, e.g. disodium succinate, is then converted to diammonium succinate through ion substitution, for example, by the addition of ammonia. In one preferred embodiment, a disodium succinate slurry is combined with carbon dioxide and ammonia, to yield a slurry including diammonium succinate with sodium bicarbonate as a by-product.

After the diammonium succinate is formed, it is reacted with sulfate ions from a sulfate ion source to form ammonium sulfate and pure succinic acid. This can be accomplished by the addition of sulfuric acid, as the reaction is advantageously performed at a pH of less than 2, preferably between 1.5 and 1.8 to form crystalline succinic acid. Succinic acid has extremely low solubility in aqueous solutions with a pH below 2, particularly in the range of 1.5 to 1.8. In a preferred method, ammonium bisulfate is combined with the ammonium succinate to yield free succinic and ammonium sulfate. The succinic acid can be filtered from the product stream including the ammonium sulfate and further purified by the addition of methanol. Any remaining sulfates will be insoluble in methanol, whereas the succinic acid will be substantially dissolved in the methanol. After methanol is evaporated, substantially pure crystalline succinic acid remains. The evaporated methanol can be condensed and reused.

The ammonium sulfate can be readily cracked at a temperature of about 300° C., to form a combination of ammonium bisulfate and ammonia gas. A sulfate salt of the base can be another by-product. In the two-step conversion, sodium bicarbonate given off during the conversion of disodium succinate to diammonium succinate can be recycled into the fermenter to maintain a neutral pH and thereby decrease the need for added sodium hydroxide.

As examples of providing advantageous fermentation processes for producing high purity carboxylic acids and improved purification methods, a series of operations for converting diammonium succinate (either from the fermenter or from the conversion of disodium succinate) to succinic acid and for crystallizing the acid to obtain a high purity product are provided. These operations are also schematically presented in the flow diagrams of FIGS. 1 and 2, for added clarity. In the methods of the preferred embodiments, the use of additional reagents are minimized and the amount of waste by-products are relatively low. In addition the reagents in certain preferred embodiments are regenerated within the process and only makeup amounts are needed.

In preferred embodiments of the invention, two important physical attributes are employed to separate succinic acid from other process material. First, the minimal solubility of succinic acid in water in the presence of sulfuric acid or hydrogen sulfate ions is used to separate succinic acid from the sulfates. Second, sulfates are virtually insoluble in methanol, although methanol is a good solvent for succinic acid. Therefore, this attribute is used to separate the sulfates for recycling and to further purity succinic acid without sulfate impurities.

Aspects and attributes of the invention will be exemplified with reference to the following examples, which are provided for purposes of illustration only, and are not intended to be construed in a limiting sense.

EXAMPLE 1

The Production of Succinic Acid from Diammonium Succinate

Referring generally to FIG. 1, carbohydrates (such as corn derived carbohydrates, such as glucose) are anaerobically fermented in Fermenter 101 with a microorganism that is capable of or genetically engineered to produce succinic acid. One especially suitable organism is identified as E. Coli AFP-111 (American Type Culture Collection ATCC 202021) Fermenter 101 is run under controlled conditions with the required biomass nutrients, carbon dioxide, and ammonia to produce a high yield of succinate. (See, e.g. U.S. application Ser. No. 08/556,805, filed Nov. 2, 1995, the contents of which are incorporated herein by reference). A pH of over 6.0, preferably at about 7 is preferred.

Recycled ammonia (Stream 18) from a thermal cracker 102 is advantageously added to fermenter 101 to neutralize the succinic acid produced by the microbe to diammonium succinate. Additional ammonia, if required, can be made up by the addition of ammonium hydroxide. The neutralization is carried out to maintain a substantially neutral pH where anaerobic fermentation is commonly most productive. The output from fermenter 101 will generally be a dilute (6–10% w/w) aqueous diammonium succinate solution (Stream 1) that contains a number of insoluble impurities such as dead cells and proteins.

Stream 1 is preferably filtered with a filter 103 to remove the insolubles. The filtrate (Stream 2) will generally be a dilute (~10% w/w) solution that is preferably concentrated to maximize the efficiency of the subsequent separation processes. An evaporator, such as a multi-effect evaporator 104 can be used to concentrate the solution to about 25–30% w/w ammonium succinate. This concentrated solution, with a pH of about 7.0 (Stream 3), can then be fed into a crystallizer 105 to which a source of sulfate ions, here, recycled ammonium bisulfate (Stream 17) is added. This addition serves to reduce the pH of the solution to approximately 1.5–1.8. At this low pH, the succinate ion is protonated by ammonium bisulfate to form ammonium sulfate and succinic acid.

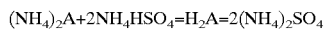

$$(NH_4)_2A + 2NH_4HSO_4 = H_2A = 2(NH_4)_2SO_4$$

where A=succinate anion=(HOOC) (CH$_2$)$_2$ (COOH)

Succinic acid crystallizes due to its low solubility at this pH. The desired pH (under 2, preferably 1.5–1.8) can also be obtained by a makeup stream of fresh ammonium bisulfate or sulfuric acid. The amount of ammonium bisulfate added is important to maintain the pH between 1.5 and 1.8 because optimal yield is generally obtained in this pH range. The resulting slurry (Stream 4) can then be filtered with a filter 106 and washed.

The crystalline succinic acid (Stream 5) is then advantageously dissolved in methanol (Stream 10) in a methanol purification station 107 to separate succinic acid from any sulfates that may co-crystallize with succinic acid. The sulfates (Stream 8), if any, are relatively insoluble in methanol and can be filtered out and combined with Stream 12 for thermal cracking. It is believed that other alcohols can be used, but that methanol yields the best results. The methanol from the succinic acid/methanol solution (Stream 6) can then be evaporated in an evaporator 108 to produce pure crystalline succinic acid (Stream 7). The evaporated methanol (Stream 9) can be collected and stored for recycling in a methanol storage tank 109.

Methanol (Stream 15) can be added to the filtrate (Stream 11) which contains ammonium sulfate and residual succinic acid, ammonium bisulfate, and sulfuric acid in a crystallizer 110. The methanol causes substantially all the sulfates to crystallize out of solution. The crystallized sulfates are advantageously separated by filtration 110. This crystallization occurs because the sulfates are virtually insoluble in methanol. This step enables the separation of the sulfates from any residual succinic acid, and can reduce the presence of charred organics in the subsequent sulfate cracking operation.

The sulfates (Stream 12) containing mostly ammonium sulfate and some residual ammonium bisulfate and sulfuric acid can then be fed into thermal cracker 102 which can be maintained at about 200–310° C., preferably about 290–310° C., most preferably about 300° C. At this tem perature range, ammonium sulfate cracks to produce ammonia and ammonium bisulfate. Formation of sulfuric acid is also possible.

$$(NH_4)_2SO_4 \rightarrow NH_4HSO_4 + NH_3$$

Ammonium bisulfate, the residual sulfuric acid and residual uncracked ammonium sulfate (Stream 17) can be recycled back to succinic acid crystallizer 105. Ammonia can be fed back to fermenter 101 to provide the base value for neutralization (Stream 18).

The filtrate from crystallizer (Stream 13) containing methanol, water and residual succinic acid can be distilled in a methanol separator 111, to separate methanol from the aqueous media. The methanol (Stream 14) can be stored for recycling or fed directly to tank 109. The bottom product of the distillation (Stream 16), which is an aqueous solution containing residual succinic acid and some sulfates can be combined with Stream 2 for concentration.

Crystalline succinic acid is substantially the only product generated by this process.

EXAMPLE 2

Production of Succinic Acid from Disodium Succinate

Figure 2:
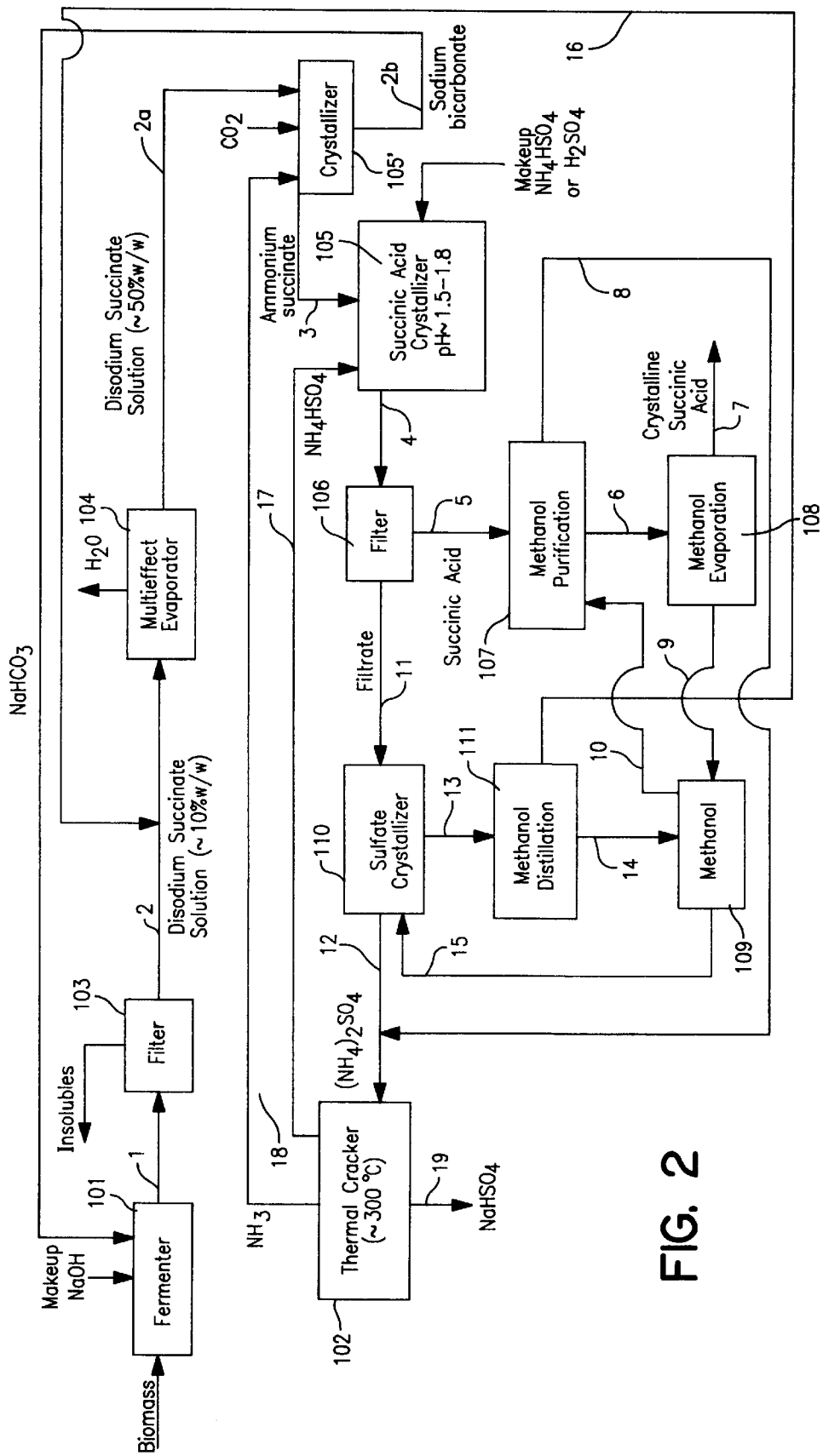
FIG. 2 is a schematic block process flow diagram for the production of succinic acid from disodium succinate, in accordance with another preferred embodiment of the invention.

Referring generally to FIG. 2, carbohydrates, such as corn derived carbohydrates, such as glucose, are anaerobically fermented with a microorganism that produces succinic acid. The fermenter is advantageously run under controlled conditions with the required biomass, nutrients, carbon dioxide, and a base to produce a high yield of succinate. The same stream numbers and other reference numerals recited with reference to Example 1 and FIG. 1 will be repeated where the stream or functional element in FIG. 2 is similar in nature to that of FIG. 1, even if the two are not exactly identical.

Recycled sodium bicarbonate (Stream 2b) is added to fermenter 101 to maintain a neutral pH broth for optimum production. The bicarbonate for the anaerobic conditions of the fermenter is also provided by this stream. Additional base, if required, can be made up by the addition of sodium hydroxide, for example. Bases with other cations besides sodium can be used. However, it has been observed that the monovalent cations such as potassium, yield the best results. The output from fermenter 101 will typically be a dilute (6–10% w/w) aqueous disodium succinate solution (Stream 1) that contains a number of insoluble impurities such as dead cells and proteins.

Stream 1 should be filtered to remove the insolubles with filter 103. The filtrate (Stream 2) is preferably concentrated to maximize the efficiency of the subsequent separation processes. Multieffect evaporator 104 can be used to concentrate the solution to near saturation (50% w/w). This concentrated solution, having a pH of generally about 7.0 (Stream 2a), is fed into a crystallizer 105' to which recycled ammonia (Stream 18) and carbon dioxide can be added. This will convert the disodium succinate to diammonium succinate (Stream 3) with the formation of solid sodium bicarbonate (Stream 2b). The conversion of disodium succinate to diammonium succinate in crystallizer 105 using ammonia and carbon dioxide is a modification of the Solvay process used to produce sodium carbonate (See Rauh, Supra, the contents of which are incorporated herein by reference.).

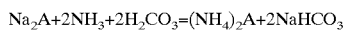

where A=succinate anion=(HOOC) $(CH_2)_2$(COOH)

Solid sodium bicarbonate (Stream 2b) is advantageously recycled back into the fermenter as the base reagent.

As stated above, the streams in Example 2 are substantially the same as those of Example 1, with the goal of producing diammonium succinate. However, one difference is in stream 18. In FIG. 2, ammonia produced by cracking (Stream 18) is recycled for the conversion of disodium succinate to diammonium succinate. In Example 1, the ammonia of stream 18 is recycled to the fermenter.

Diammonium succinite from crystallizer 105' is converted to crystalllized succinic acid in crystallizer 105 by the addition of $NH_4$ $HSO_4$ (Stream 17) from thermal cracker 102.

Crystalline succinic acid and some sodium bisulfate (by-product) is produced in this process.

The following experiments were performed to demonstrate the feasibility of the processes described above.

EXAMPLE 3

Determination of the Succinic Acid Solubility in Aqueous

Ammonium Bisulfate Solutions at 23° C. (Experiment I)

This example demonstrates an optimum pH range to obtain the maximum yield for succinic acid in crystallizer 105.

Figure 3:
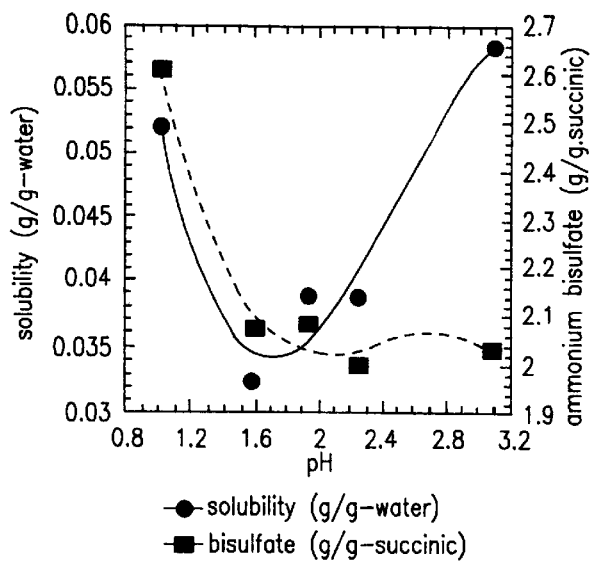
FIG. 3 is a graph showing change in succinic acid solubility (g/g—water) in aqueous ammonium bisulfate solutions as a function of pH.
Figure 4:
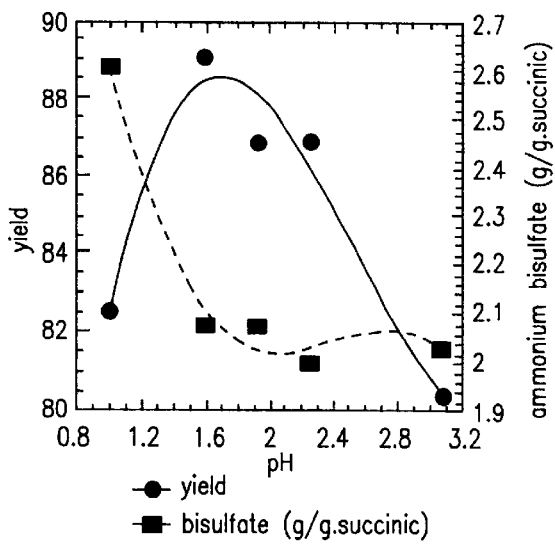
FIG. 4. Is a graph showing change in succinic acid yield in aqueous ammonium bisulfate solutions as a function of pH.

20 g of succinic acid was slurried in 50 ml of water. The slurry was neutralized (pH=7) by adding 29 ml of 58% ammonium hydroxide. The total volume of this solution was 87 ml. Five 20 ml fractions, each containing 4.6 g of succinic acid, were prepared from the solution. The pH of the five fractions was adjusted with ammonium bisulfate to determine the solubility of succinic acid in aqueous ammonium bisulfate solutions. The results are presented in FIGS. 3 and 4.

The data suggests that the optimum pH range for maximum yield is 1.2 to 2.5, preferably below 2, more preferably about 1.5–1.8.

EXAMPLE 4

Determination of Ammonium Sulfate Solubility in Methanol-Water Solutions at 23° C. (Experiment II)

Figure 5:
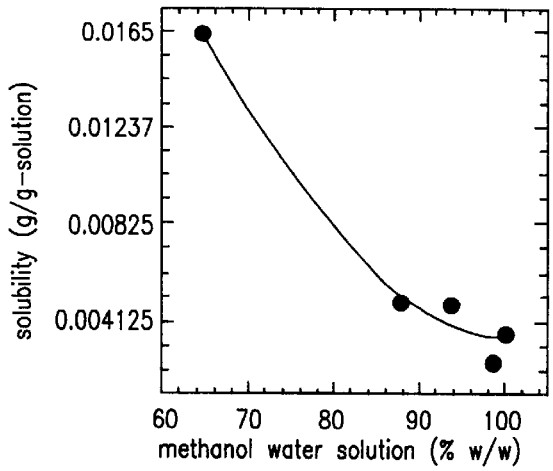
FIG. 5 is a graph showing the change in solubility of ammonium sulfate in methanol-water solutions.

Ammonium Sulfate in excess was slurried for 24 hr. in methanol-water solutions of different proportions. Residual weight determinations resulted in the solubility curve given in FIG. 5. The data suggests that sulfates are virtually insoluble in methanol-water solutions with high methanol content.

EXAMPLE 5

Determination of Ammonium Sulfate Solubility in Water at 23° C. (Experiment III)

Ammonium sulfate in excess was slurried in water for 24 hr. The solubility calculated based on the residual weight was 43.8% w/w.

EXAMPLE 6

Preliminary Process Simulation

Operations involving Streams 3, 4, 5, 11, 12, 13 and 15 in FIGS. 1 and 2 were simulated based on the data collected in Experiments I, II and III. From Experiment I, a pH value of 1.6 was chosen as the target pH for the crystallization of succinic acid. From Experiment II, 80% w/w methanol solution was chosen as the target methanol-water ratio for the crystallization of sulfates. Using the results of Experiment III, the initial concentration of ammonium succinate was chosen such that there would have been sufficient water to solubalize ammonium sulfate produced in the conversion of ammonium succinate into succinic acid. This precaution was taken to minimize contamination of succinic acid by sulfates.

Stream 3: An aqueous solution containing 25.4 g of ammonium succinate and 61.3 g of water (28.6% w/w, ammonium succinate) was prepared. Stoichiometrically, 25.4 g of ammonium succinate is expected to produce 20 g of succinic acid.

Ammonium bisulfate was added, stepwise, to adjust the solution pH to 1.6. The total amount of ammonium bisulfate added was 38.5 g. According to FIGS. 3 and 4, the ammonium bisulfate requirement is 41.4 g. The agreement between the added amount and the required amount is reasonable.

Stream 5: The above pH adjustment resulted in a succinic acid slurry. The slurry was filtered and the crystalline succinic acid was dried at 70° C., overnight. According to FIG. 3, at 89% yield, Stream 5 should have produced about 17.8 g of succinic acid. However, the actual amount was 18.7 g suggesting the possibility of sulfate contamination. Elemental analysis for sulfur and nitrogen indicated the presence of approximately 0.5 g of sulfates in the product. Since a pure product is desirable, using more water in Stream 3 to keep sulfates soluble was deemed advisable. In addition, a purification step using methanol was incorporated (Streams 5 and 10).

Streams 11 and 15: 245 g of methanol was added to the filtrate (Stream 11) from the succinic acid filtration. Methanol was added such that the mixed solvent composition corresponded to the predetermined 80% w/w methanol solution. This produced 38.4 g of crystalline sulfates. The expected amount of sulfates was 41.7 g. The discrepancy between the experimental yield and the calculated yield is not unreasonable.

EXAMPLE 6

Thermal Cracking of Ammonium Sulfate

The conversion of ammonium succinate to succinic acid using ammonium bisulfate produces ammonium sulfate. Thermal cracking of ammonium sulfate, in turn, produced ammonium bisulfate that can be recycled for use in succinic acid crystallization.

A rotary tube furnace was used for thermal cracking. The furnace was attached to an aspirator to vent the effluent gasses. The rotary tube furnace was preheated to 300° C. 20 g of ammonium sulfate was cracked for 1 hr and 17.8 g of cracked sulfates were collected. Stoichiometrically, 17.4 g of ammonium bisulfate is expected from 20 g of ammonium sulfate. On a mass basis, the experimental amount and the calculated amount was in agreement. Therefore, these conditions were deemed appropriate for cracking of ammonium sulfate.

Based on the results presented above, a process for the separation of succinic acid was simulated between Streams 3 and 17. Three cycles of the process were conducted.

EXAMPLE 7

Determination of Succinic Acid Solubility in Methanol at 23° C.

Succinic acid in excess was slurried in methanol for 24 hr. The solubility was calculated based on the residual weight was 16.5 g of succinic acid in 79 g of methanol.

The following represents a process simulation, which is presented for purposes of illustration only and is not intended to be construed in a limiting sense.

EXAMPLE 8

Cycle 1:

A 25.6% w/w aqueous solution of ammonium succinate (Stream 3) was prepared by neutralizing a slurry containing 20 g of succinic acid and 55 g of water with 27.5 g of 58% w/w ammonium hydroxide.

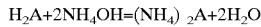

$$H_2A + 2NH_4OH = (NH_4)_2A + 2H_2O$$

where A=succinate anion=(HOOC) $(CH_2)_2$ (COOH)

The ammonium succinate solution could have been prepared by dissolving 25.4 g ammonium succinate in 74 g of water.

The aqueous solution of ammonium succinate, with a pH of 7.0, was taken in a crystallizer and 39 g of ammonium bisulfate was added, resulting in a pH adjustment to 1.6 and the crystallization of succinic acid.

The resulting slurry (Stream 4) was filtered. The separated crystalline succinic acid (Stream 5) was dried overnight at 70° C. The dry weight was 16.5 g.

The crystalline succinic acid (Stream 5) was dissolved in 79 g of methanol (Stream 10) to separate the succinic acid from any sulfates that may have co-crystallized with succinic acid. The undissolved sulfates (Stream 8) were filtered, dried and stored for thermal cracking. The dry weight of the sulfates was 0.9 g. Therefore, the weight of the succinic acid dissolved in methanol was 15.6 g. This amount corresponds to a yield of 78% (Stream 7). The low yield was expected since this was the initial cycle.

Two hundred eighty six grams of methanol (Stream 15) was added to the filtrate (Stream 11) containing ammonium sulfate and any residual succinic acid, ammonium bisulfate, and sulfuric acid in a crystallizer. The resulting slurry was filtered. The crystalline sulfates were dried overnight at 70° C. The dry weight was 40.3 g at a yield of 90.1%. The theoretical yield was 93.6%.

The sulfates (Stream 12) containing mostly ammonium sulfate and some residual ammonium bisulfate and sulfuric acid were added to a thermal cracking unit maintained at 300° C. for 50 minutes. During the cracking process, the molten sulfates turned black in color, indicating the presence of charred organic material. The molten sulfates were cooled to room temperature. During cooling, 50 ml of water was added to dissolve the sulfates. The solution containing the charred material was filtered with a 0.2 micron filter. The charred material was discarded. The clear solution was evaporated down to about 40 ml to concentrate the sulfates. During evaporation, some of the sulfates were lost due to an accidental spill. 190 g of methanol was added to the remaining solution. The resulting sulfate slurry was filtered and then dried at 70° C., overnight. 17.8 g of sulfates were recovered.

The filtrate was distilled to separate methanol and 166 g of methanol was collected and stored for recycling. This step, involving the separation of the sulfates from the charred material, is not shown in the process flow diagram (FIGS. 1 and 2). However, it may be necessary under certain circumstances, because some organic carryover may not be avoidable.

The filtrate (Stream 13) containing methanol, water and residual succinic acid was distilled to separate methanol from the aqueous media and 250 g of methanol (Stream 14) was collected and stored for recycling. The bottom product of the distillation (Stream 16), which is an aqueous solution containing residual succinic acid and some sulfates, was evaporated down to a 60 ml solution. The solution was evaporated down to 60 ml so that the solution, along with fresh succinic acid, will make a solution consisting of approximately 25–30% w/w ammonium succinate (Stream 3) upon neutralization. This preparation mimics the concentration of Streams 2 and 16 by evaporation to make Stream 3 in the case of the process envisioned for the production of succinic acid from diammonium succinate (FIG. 1). Similarly, the preparation mimics the concentration of Streams 2 and 16 by evaporation to make Stream 2a in the case of the process envisioned for the production of succinic acid from disodium succinate (FIG. 2). In both cases, Stream 16 recycles residual succinic acid to maximize the yield.

EXAMPLE 9

Cycle II:

The concentrated Stream 16 from Cycle I was combined with 16.5 g of fresh succinic acid. The resulting slurry was neutralized with 28.5 ml of 58% w/w ammonium hydroxide.

The aqueous solution of ammonium succinate, with a pH of 7.00, was taken in a crystallizer and 17.8 g of recycled ammonium bisulfate (Stream 17) and 33.2 g of fresh ammonium bisulfate was added. The acidification resulted in a pH adjustment to 1.45 and the crystallization of succinic acid. The addition of ammonium bisulfate exceeded the theoretical requirement by approximately 10 g. One contributing factor may be the severe hygroscopicity of ammonium bisulfate. The additional weight may be due to the hydration of recycled and fresh ammonium bisulfate. During these experiments, no precautions were taken to avoid hydration of ammonium bisulfate. Also, the reduction of the pH of the succinic acid slurry exceeded the optimal value of 1.6. The pH value reached 1.45 requiring more ammonium bisulfate. This outcome was not intentional.

The resulting slurry (Stream 4) was filtered. The separated crystalline succinic acid (Stream 5) was dried overnight at 70° C. The dry weight was 19.4 g. Theoretically, 16.5 g was expected. This outcome indicated the presence of some carryover sulfates in the succinic acid stream.

The crystalline succinic acid (Stream 5) containing some sulfates was dissolved in 79 g of methanol (Stream 10) to separate the succinic acid from the sulfates that co-crystallized with succinic acid. The undissolved sulfates (Stream 8) were filtered, dried and stored for thermal cracking. The dry weight of the sulfates was 4 g. Therefore, the weight of the succinic acid dissolved in methanol was 15.4 g. This amount corresponds to a yield of 93.3% yield (Stream 7).

Two hundred eighty six grams of methanol (Stream 15) was added to the filtrate (Stream 11) containing ammonium sulfate and any residual succinic acid, ammonium bisulfate, and sulfuric acid in a crystallizer. The resulting slurry was filtered. The crystalline sulfates were dried overnight at 70° C. The dry weight was 47.5 g at a yield of 83.6%. Accounting for the 4 g of undissolved sulfates in Stream 8, the yield increases to 90.7%. The theoretical yield was 94.9%. The discrepancy between the actual and the theoretical yield may be due to the addition of hydrated ammonium bisulfate that results in an overestimation for the sulfates present in the system.

The sulfates (Stream 12) containing mostly ammonium sulfate and some residual ammonium bisulfate and sulfuric acid were added to a thermal cracking unit maintained at 300° C. for 55 minutes. During the cracking process, the molten sulfates turned black in color, indicating the presence of charred organic material. The molten sulfates were cooled to room temperature. During cooling, 50 ml of water was added to dissolve the sulfates. The solution containing the charred material was filtered with a 0.2 micron filter. The charred material was discarded. The clear solution was evaporated down to about 40 ml to concentrate the sulfates. 198 g of methanol was added to the solution. The resulting sulfate slurry was filtered and then dried at 70° C., overnight. The dry weight of the sulfates was 25 g. The filtrate was distilled to separate methanol and 154 g of methanol was collected and stored for recycling.

The filtrate (Stream 13) containing methanol, water and residual succinic acid was distilled to separate methanol from the aqueous media and 250 g of methanol (Stream 14) was collected and stored for recycling. The bottom product of the distillation (Stream 16), which is an aqueous solution containing residual succinic acid and some sulfates was evaporated down to a 60 ml solution.

EXAMPLE 10

Cycle III:

The concentrated Stream 16 from Cycle II was combined with 17.7 g of fresh succinic acid. The resulting slurry was neutralized with 28.5 ml of 58% w/w ammonium hydroxide.

The aqueous solution of ammonium succinate was taken in a crystallizer and 25 g of recycled ammonium bisulfate (Stream 17) and 25.5 g of fresh ammonium bisulfate was added. The acidification resulted in a pH adjustment to 1.6 and the crystallization of succinic acid. As in Cycle II, the addition of ammonium bisulfate exceeded the theoretical requirement by approximately 10 g.

The resulting slurry (Stream 4) was filtered. The separated crystalline succinic acid (Stream 5) was dried overnight at 70° C. The dry weight was 24.5 g. Theoretically, 17.7 g was expected. This outcome indicated the presence of some carryover sulfates in the succinic acid stream. The crystalline succinic acid (Stream 5) containing some sulfates was dissolved in 79 g of methanol (Stream 10) to separate the succinic acid from the sulfates that co-crystallized with succinic acid. The undissolved sulfates (Stream 8) were filtered, dried and stored for thermal cracking. The dry weight of the sulfates was 7.7 g. Therefore, the weight of the succinic acid dissolved in methanol was 16.8 g. This amount corresponds to a yield of 94.9% yield (Stream 7).

Two hundred seventy six grams of methanol (Stream 15) was added to the filtrate (Stream 11) containing ammonium sulfate and any residual succinic acid, ammonium bisulfate and sulfuric acid in a crystallizer. The resulting slurry was filtered. The crystalline sulfates were dried overnight at 70° C. The dry weight was 46.7 g at a yield of 83%. Accounting for the 7.7 g of undissolved sulfates in Stream 8, the yield increases to 96.7%. The theoretical yield was 94.9%.

The sulfates (Stream 12) containing mostly ammonium sulfate and some residual ammonium bisulfate, and sulfuric acid were added to a thermal cracking unit maintained at 300° C. for 50 minutes. During the cracking process, the molten sulfates turned black in color indicating the presence of charred organic material. The molten sulfates were cooled to room temperature. During cooling, 50 ml of water was added to dissolve the sulfates. The solution containing the charred material was filtered with a 0.2 micron filter. The charred material was discarded. The clear solution was evaporated down to about 45 ml slurry to concentrate the sulfates. Added 237 g of methanol to the slurry. The resulting sulfate slurry was filtered and then dried at 70° C., overnight. The dry weight of the sulfates was 28.3 g. The filtrate was distilled to separate methanol and 225 g of methanol was collected and stored for recycling.

The filtrate (Stream 13) containing methanol, water and residual succinic acid was vacuum distilled to separate methanol from the aqueous media and 190 g of methanol (Stream 14) was collected and stored for recycling. The 37 ml bottom product of the vacuum distillation (Stream 16), which is an aqueous solution containing residual succinic acid and some sulfates was topped to a 60 ml solution with water.

EXAMPLE 11

Glucose from corn derived carbohydrates was anaerobically fermented with a microorganism (ATCC Accession No. 29305, American Type Culture Collection, 12301 Parklawn Drive, Rockville, MD 20852). Ammonia, as a neutralizing base, is added to the fermenter to neutralize succinic acid produced by the microbe into diammonium succinate. Output from the fermenter is a dilute (6–10% w/w) aqueous diammonium succinate solution, containing impurities. The stream is filtered to remove insolubles and was concentrated in a multi-effect evaporator to about 30% w/w. The concentrated solution with the pH of about 7 is fed into a succinic acid crystallizer, to which ammonium bisulfate is added to reduce the pH to between 1 and 2. Sulfuric acid can also be added at this point. The amount of ammonium bisulfate and/or sulfuric acid is determined by monitoring the solutions pH.

Crystallized succinic acid is filtered out to yield approximately 90% succinic acid on a weight basis. The filtrate containing ammonium sulfate, ammonium bisulfate and sulfuric acid is fed to a thermal cracking unit at approximately 300° C. Output from the thermal cracker is ammonia and ammonium bisulfate. The ammonium bisulfate and residual sulfuric acid are recycled back to the succinic acid crystallizer. Ammonia is fed from the thermal cracking unit to the fermenter.

EXAMPLE 12

Glucose is fermented with an organism producing succinic acid. Sodium bicarbonate is used as a neutralizing base to maintain a pH of approximately 7. The output is a 6–10% w/w aqueous disodium succinate solution. The stream is filtered and then concentrated to near saturation (50% w/w). This concentrate solution, having a pH of about 7.0 is fed into a crystallizer, to which ammonia (preferably recycled ammonia) and carbon dioxide are added. This converts the disodium succinate into diammonium succinate, with the formation of solid sodium bicarbonate. The bicarbonate can be recycled back into the fermenter as the neutralizing base.

The diammonium succinate is then fed to a succinic acid crystallizer, to which ammonium bisulfate is added, to reduce the pH to a range of about 1.0 to 2.4. Sulfuric acid can also be added at this point to lower the pH. This process yields approximately 90% succinic acid on a weight basis. The filtrate, resulting from the filtration of the succinic acid slurry, containing a mixture of ammonium sulfate and ammonium bisulfate and sulfuric acid is fed to a thermal cracking unit at about 300° C.

The method of the invention involves providing a solution with a succinate salt, concentrating the solution advantageously to near saturation, acidifying the solution to a pH between about 1.0 and 2.5 in the presence of sulfate ions, such as through the addition of ammonium bisulfate or sulfuric acid to yield crystallized succinic acid. The difference in solubility between sulfates and succinic acid in alcohol such as methanol can be used to further purify and separate succinic acid from the product streams. If metal salts, such as disodium succinate, the material can be combined with ammonia and carbon dioxide at a neutral pH to precipitate sodium bicarbonate, which can be recycled for use in raising the pH of the fermentation broth.

As discussed above, a cracking step can be employed, wherein the filtrate waste from the acidification step contains ammonium sulfate, ammonium bisulfate and sulfuric acid. The filtrate waste is fed into a thermal cracking unit, operating in the range of about 290 to 310° C., to produce ammonia and ammonium bisulfate, which can be recycled for use in earlier process steps.

A sulfate crystallizing step can be added after the acidifying step, wherein methanol is added to the slurry, causing crystallization of sulfates and dissolving the crystal in succinic acid, to form a methanol/succinic acid solution. Sulfate solids can be filtered out and cracked at about 300° C. The succinic acid can be crystallized from the methanol solution through evaporation. The evaporated methanol can be condensed and recycled for further use.

It can thus be seen that the present invention provides a process for converting either succinate salts, such as metal succinates or diammonium succinate into succinic acid and the step for further purifying the succinic acid involving alcohol dissolutions in preferably methanol.

It will thus be seen that the objects set forth above, among those made apparent form the preceding description, are efficiently attained and, since certain changes may be made in carrying out the above method and in the composition set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A method of producing succinic acid, comprising the steps of:
   providing an aqueous solution including succinate ions; and adding a source of sulfate ions to the aqueous solution and lowering the pH of the aqueous solution sufficiently to crystallize succinic acid from the aqueous solution; and
   removing the succinic acid.

2. The method of claim 1, wherein ammonium ions are added to the solution.

3. The method of claim 2, including the step of forming a succinate salt and then substituting an ammonium ion for the cation of the succinate salt.

4. The method of claim 3, wherein the cation of the succinate salt is an alkali metal ion.

5. The method of claim 3, wherein the cation is the sodium ion.

6. The method of claim 1, wherein the source of sulfate ions comprises ammonium sulfate.

7. The method of claim 4, wherein the source of sulfate ions comprises ammonium sulfate.

8. The method of claim 1, wherein the succinate ions are is provided by fermenting a carbohydrate in a fermentation broth in a fermenter with an organism which produces succinic acid and adding at least one base to the fermentation broth during fermentation.

9. The method of claim 8, wherein the base comprises ammonia.

10. The method of claim 8, wherein the base comprises sodium bicarbonate.

11. The method of claim 8, wherein the at least one base reacts with succinic acid to yield diammonium succinate.

12. The method of claim 8, wherein the base is an alkai metal hydroxide which reacts with the succinic acid to form a succinate salt.

13. The method of claim 11, wherein the source of sulfate ions comprises ammonium bisulfate.

14. The method of claim 6, wherein ammonium bisulfate is reacted with ammonium succinate to yield crystallized succinic acid and ammonium sulfate, and the ammonium sulfate is cracked to yield ammonia and ammonium bisulfate and at least a portion of the ammonium bisulfate yielded is used to react with additional ammonium succinate.

15. The method of claim 7, wherein ammonium bisulfate is reacted with ammonium succinate to yield crystallized succinic acid and ammonium sulfate, and the ammonium sulfate is cracked to yield ammonia and ammonium bisulfate and at least a portion of the ammonium bisulfate yielded is used to react with additional ammonium succinate.

16. The method of claim 1, wherein the pH is lowered to about 1.2 to 2.5.

17. The method of claim 1, wherein the pH is lowered to about 1.5 to 1.8.

18. The method of claim 1, wherein the removed succinic acid is dissolved in alcohol, the combination of succinic acid and alcohol is filtered, and the alcohol evaporated.

19. The method claim of claim 18, wherein the alcohol is methanol.

20. A method of producing succinic acid, comprising the steps of:
    providing a succinic acid salt; and
    reacting the succinic acid salt with a source of sulfate ions at sufficiently low pH to yield crystalline succinic acid.

21. The method of claim 20, including the steps of dissolving the succinic acid in methanol liquid and then filtering the solids from the liquid; and separating the succinic acid from the liquid.

22. The method of claim 21, wherein the separation is done by evaporation.

23. The method of claim 20, wherein the sulfate source is ammonium bisulfate.

24. The method of claim 20, wherein the pH is lowered to below about 2.0.

25. The method of claim 20, wherein the pH is lowered to about 1.5–1.8.

* * * * *